(12) United States Patent
Castaldi et al.

(10) Patent No.: US 7,329,751 B2
(45) Date of Patent: Feb. 12, 2008

(54) PROCESS FOR THE PREPARATION OF CLOPIDOGREL

(75) Inventors: Graziano Castaldi, Briona (IT); Giuseppe Barreca, Montevecchia (IT); Alberto Bologna, Crema (IT)

(73) Assignee: Dipharma S.p.A., Mereto Di Tompa (IT)

( * ) Notice: Subject to any disclaimer, the term of this patent is extended or adjusted under 35 U.S.C. 154(b) by 418 days.

(21) Appl. No.: 10/513,156

(22) PCT Filed: Apr. 22, 2003

(86) PCT No.: PCT/EP03/04179

§ 371 (c)(1),
(2), (4) Date: Nov. 2, 2004

(87) PCT Pub. No.: WO03/093276

PCT Pub. Date: Nov. 13, 2003

(65) Prior Publication Data

US 2005/0143414 A1    Jun. 30, 2005

(30) Foreign Application Priority Data

May 3, 2002    (IT) .......................... MI2002A0933

(51) Int. Cl.
*C07D 471/02* (2006.01)
(52) U.S. Cl. .................................... 546/114
(58) Field of Classification Search ................ 546/114
See application file for complete search history.

(56) References Cited

U.S. PATENT DOCUMENTS 4,529,596 A * 7/1985 Aubert et al. ............ 514/233.8

FOREIGN PATENT DOCUMENTS

WO         99/18110        4/1999

* cited by examiner

*Primary Examiner*—Amelia A. Owens
(74) *Attorney, Agent, or Firm*—Young & Thompson

(57) ABSTRACT

A process for the preparation of clopidogrel (1)

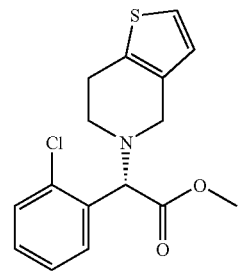

(1)

by reaction of the N,N'-bis-4,5,6,7-tetrahydro-[3,2-c]-thienopyridyl methane (12)

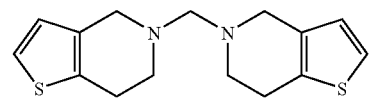

(12)

with (R)-2-chlorophenylacetic acid derivatives of formula (13)

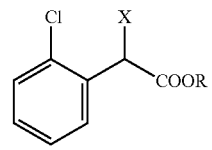

(13)

in which X and R have the meanings as indicated in the disclosure.

10 Claims, No Drawings

PROCESS FOR THE PREPARATION OF CLOPIDOGREL

The present invention relates to antiplatelet and antithrombotic agents, more particularly to a process for the preparation of clopidrogrel (1): methyl [(S)-2-(2-chlorophenyl)-2-(4,5,6,7-tetrahydrothieno[3,2-c]-pyridyl)acetate.

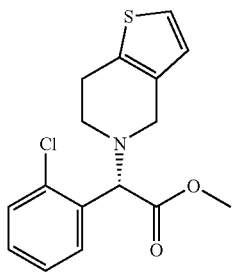

(1)

PRIOR ART

Clopidogrel (1) is a compound having antiplatelet and antithrombotic activities first described by Aubert et al. (EP 0 099 802 and U.S. Pat. No. 4,529,596) and synthesized by reaction between 4,5,6,7-tetrahydro[2,3-c]thienopyridine (2) and 2-chloro-2-(2'-chlorophenyl)acetic acid methyl ester (3) (scheme 1).

Scheme 1

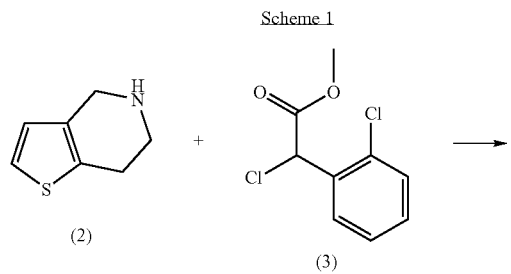

According to this process, the product is obtained as a racemic mixture. The separation of the two enantiomers can be carried out with optical resolution procedures as disclosed in EP 0281 459, but this involves a remarkable decrease in yields.

A method overcoming said drawback has been suggested in WO 98/51689, in which clopidrogrel is prepared by reacting 2-(2-thienyl)-ethylamine (4) with o-chlorobenzaldehyde (5) and sodium cyanide. The resulting nitrile (6) is transformed into the corresponding amide (7) and subsequently into the methyl ester (8). Intermediate (8) in the configuration suitable for the synthesis of clopidogrel, can be prepared by optical separation of the amide (7) or the ester (8) with optically active acids. Finally, the desired enantiomer of ester (8) is cyclized with formaldehyde in acid medium to give clopidogrel.

Scheme 2

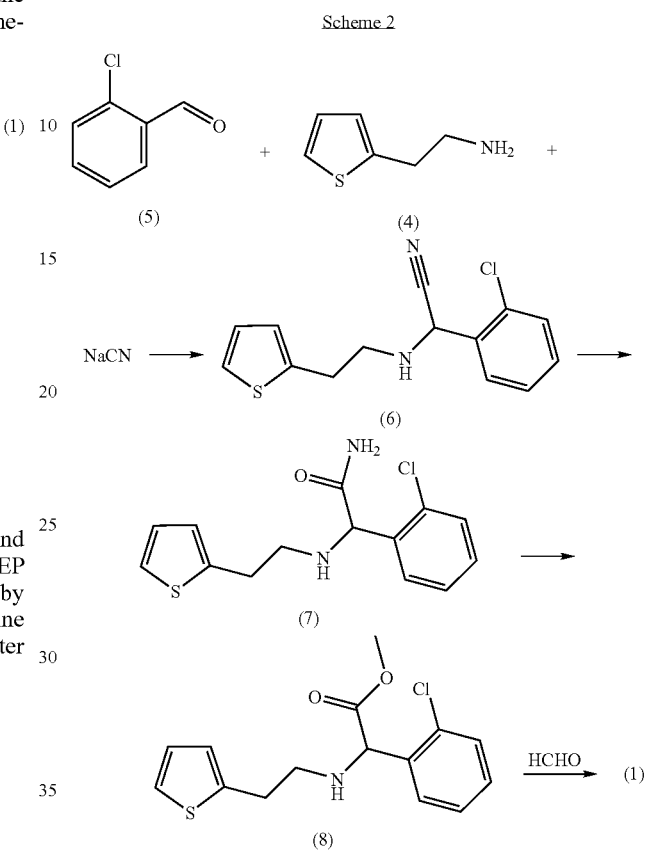

Alternatively, as disclosed in EP 466569, intermediate (8) can be obtained by reacting methyl 2-amino-(2-chlorophenyl)acetate (9) with a 2-(2-thienyl)ethanol derivative (10), in which X is halogen or a sulfonic group (scheme 3)

Scheme 3

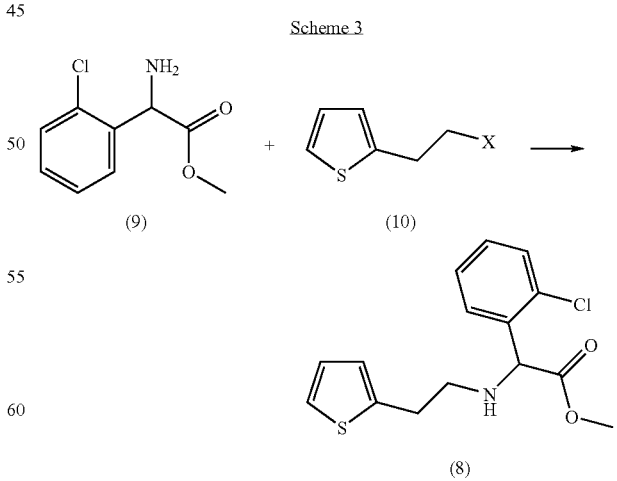

or by reacting a methyl 2-halo-(2-chlorophenyl)acetate, for example compound (3), with 2-(2-thienyl)ethylamine (4).

Finally, WO 99/18110 discloses the preparation of clopidogrel by reacting tetrahydrothieno pyridine (2) with (R)-2-chloro mandelic acid sulfonic esters (11).

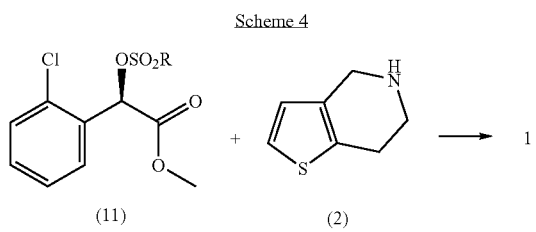

However, this method still has the disadvantage of using tetrahydro thieno pyridine, which is a low-melting solid hardly obtainable in the pure form.

DETAILED DISCLOSURE OF THE INVENTION

It has now been found that clopidogrel (1), or a pharmaceutically acceptable salt thereof, can be prepared by reacting N,N'-bis-4,5,6,7-tetrahydro-[3,2-c]-thienopyridyl methane (12)

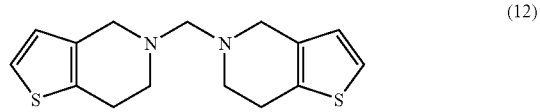

with a (R)-2-chlorophenylacetic acid derivative of formula (13)

wherein:
R is a hydrogen atom or a straight or branched $C_1$-$C_4$ alkyl group, and X is:
  a halogen selected from fluorine, chlorine, bromine and iodine, preferably bromine or chlorine;
  a $OSO_2R^1$ group wherein $R^1$ is a straight or branched $C_1$-$C_4$ alkyl group, optionally substituted with one or more halogen atoms, a straight or branched $C_1$-$C_8$ perfluoroalkyl group, an aromatic ring optionally substituted with one or more halogen atoms, straight or branched $C_1$-$C_4$ alkyl groups, or nitro groups;
  a $OCOR_1$ ester group in which $R^1$ has the meanings defined above;
  a —$ONO_2$ group;
  a $OP(OR)_2$ phosphite group or a $OPO(OR)_2$ phosphate group, in which R has the meaning as defined above; and, if desired, salifying a compound of formula (I).

When $R^1$ is a substituted alkyl group or aromatic ring, it is preferably substituted by 1 to 3 substituents as defined above, which may be the same or different.

Preferred compounds of formula (13) are (R)-2-(2-chlorophenyl)-2-(4-nitrobenzenesulfonyloxy)acetic acid methyl ester (13a) and (R)-2-bromo-2-(2-chlorophenyl)acetic acid methyl ester (13b).

The process for the preparation of clopidogrel according to the present invention is carried out in the presence of a protic or aprotic organic solvent and, if the case, in the presence of an organic or inorganic basic agent.

More particularly, a compound of formula (13) is added to a solution or suspension of intermediate (12) in a suitable organic solvent. The protic or aprotic organic solvent is, for instance, selected from a ketone, preferably acetone, methyl ethyl ketone and methyl isobutyl ketone, an alcohol, preferably a C1-C4 alkanol, acetonitrile, an aromatic hydrocarbon, preferably toluene, xylene and a chlorinated solvent, preferably methylene chloride, or a mixture thereof. According to a preferred embodiment of the invention, the solvent is acetone, acetonitrile or methanol. Compound of formula (12) is used in molar ratios ranging from 0.5:1 to 3:1 with respect to intermediate of formula (13), preferably ranging from 1:1 to 2:1.

When the reaction is carried out in the presence of an organic basic agent, such agent can be preferably selected from a compound of formula (12) itself, i.e. N,N'-bis-4,5,6,7-tetrahydro-[3,2-c]-thienopyridyl methane, diisopropylethyl-amine, 4-(dimethylamino)pyridine, triethylamine, 1,8-diazabicyclo[5.4.0]undec-7-ene and 1,4-diazabicyclo[2.2.2]octane. An inorganic basic agent is preferably an alkali, or alkaline-earth metal carbonate, e.g. potassium carbonate. The base can be used in molar ratios ranging from 0.5:1 to 1.5:1 with respect to compound (13), preferably in stoichiometric ratio. The reaction is carried out at a temperature ranging from 0° C. to the reflux temperature of the solvent, preferably from 20 to 70° C. After completion of the reaction the mixture is cooled at room temperature then, after the appropriate work up, the resulting crude is dissolved in acetone to give a solution from which clopidogrel can be precipitated as a salt by addition of a pharmacologically acceptable acid, for example concentrated sulfuric acid to afford clopidogrel hemisulfate.

Aminal N,N'-bis-4,5,6,7-tetrahydro-[3,2-c]-thienopyridyl methane of formula (12) is a novel compound and is also an object of the present invention. This compound is obtained by reacting commercially available 2-(2-thienyl)ethylamine (4) with aqueous formaldehyde or paraformaldehyde or trioxane in a medium acidified by organic or mineral acids (scheme 5).

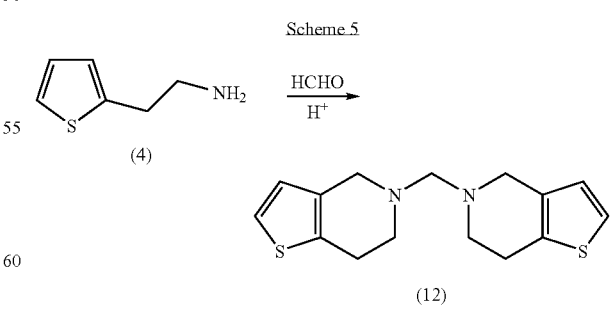

The organic acid is preferably selected from formic, acetic, trichloroacetic, trifluoroacetic, methanesulfonic, p-toluenesulfonic acids, more preferably is formic acid. A preferred mineral acid is hydrochloric acid.

When the reaction is carried out in the presence of an organic acid, this can be used as the solvent.

When the reaction is carried out in the presence of a mineral acid, water is used as the solvent. The mineral acid is usually employed in a stoichiometric amount or in excess, the mineral acid: 2-(2-thienyl)ethyl-amine (4) molar ratio preferably ranging from 1:1 to 3:1.

Formaldehyde in the form of 37% aqueous solution, paraformaldehyde or trioxane, is usually employed in molar ratios ranging from 1:1 to 1:3 with respect to 2-thienyl-ethylamine (4), preferably in a 1:1.5 ratio.

The reaction is carried out at a temperature ranging from 0° C. to the reflux temperature of the reaction mixture, preferably from 10 to 60° C.

When the reaction is completed, the acid is distilled off under vacuum or is preferably transformed into the corresponding salt by addition of a base. Preferred bases are sodium hydroxide, potassium hydroxide or ammonium hydroxide. After basifying, e.g. with an alkali metal hydroxide, intermediate (12) is recovered by filtration or extraction with suitable organic solvents. The solvent used for the extraction of intermediate (12) is preferably an aromatic hydrocarbon, more preferably toluene or xylene, or a chlorinated solvent, more preferably methylene chloride.

After removing the solvent used for the extraction, intermediate (12) is purified by crystallization from a suitable solvent. The solvent used for the crystallization of intermediate (12) can be selected from a ketone, preferably acetone and methyl isobutyl ketone, an ester, preferably ethyl acetate and butyl acetate and an alcohol, preferably methanol, ethanol and isopropanol.

An advantageous aspect of the present invention over the methods using 4,5,6,7-tetrahydro[3,2-c]thienopyridine (2), which is a low-melting solid, very soluble in the organic solvents and therefore difficult to purify by crystallization, is that compound (12) is solid and can be crystallized. Furthermore, no by-products are formed during the preparation of compound (12), conversely, following the synthetic procedures described in literature for 4,5,6,7-tetrahydro[3,2-c]thienopyridine (2), by-products form which have to be removed before carrying out the process for the preparation of clopidogrel.

The invention is illustrated in greater detail by the following examples.

EXAMPLES

Methyl (R)-2-(2-Chlorophenyl)-2-(4-nitrobenzenesulfonyloxy)acetate (13a) is prepared according to the procedure disclosed in WO 99/18110.

Example 1

Preparation of N,N"-bis-4,5,6,7-tetrahydro[3,2-c]thienopyridyl methane (12)

Method 1

2440 g of anhydrous formic acid (53.04 moles) are placed in a 3 l round-bottom flask, equipped with mechanical stirrer, thermometer and dropping funnel. 500 g of 2-(2-thienyl)ethylamine (4) (3.94 moles) are then slowly added thereto, while allowing temperature to reach 40° C. The resulting solution is cooled at room temperature, then 186.5 g of 95% paraformaldehyde (5.91 moles) are added in 10 minutes. After 14 hours at room temperature, the resulting solution is slowly poured into 6660 g of a 30% w/w sodium hydroxide solution (50 moles), while keeping temperature below 30° C. The resulting suspension is kept under stirring at room temperature for 2 hours, then the precipitated solid is recovered by filtration, washed with water and taken up into 550 ml of methanol. The obtained suspension is stirred at room temperature for 2 hours, then the solid is filtered, washed with methanol and dried under vacuum at 45° C., thereby obtaining 462 g (1.59 moles; yield: 81%) of N,N"-bis-4,5,6,7-tetrahydro-[3,2-c]-thienopyridyl methane (12) as a white crystalline solid.

$^1$H-NMR (CDCl$_3$, δ in ppm): 2.90 (m, 8H), 3.36 (s, 2H), 3.66 (s, 4H), 6.74 (d, 2H), 7.08 (d, 2H) m.p.=126.3° C.

Method 2

50 g of 2-(2-thienyl)ethylamine (4) (0.394 moles) and 250 ml of water are placed in a 500 ml round-bottom flask equipped with mechanical stirrer, thermometer and dropping funnel. 48 g of a 36% w/w hydrochloric acid aqueous solution (0.473 moles) are then slowly added and the resulting solution is heated to 50° C., then added with 47.9 g of a 37% w/w formaldehyde aqueous solution (0.591 moles) in about 20 minutes. After 5 hours at 50° C., the resulting mixture is cooled at room temperature, neutralized with 20.8 g of sodium hydroxide scales (0.52 moles) and subsequently extracted with 130 ml of toluene. The resulting organic phase is washed twice with 50 ml of water, then concentrated to a residue under reduced pressure and the resulting mixture is taken up with 100 ml of acetone, to obtain a suspension which is kept under stirring for two hours. The formed precipitate is filtered with suction and washed with acetone, thereby obtaining 26 g of N,N"-bis-4,5,6,7-tetrahydro-[3,2-c]thienopyridyl methane (12) (89.7 mmoles, yield: 45.5%) as a white solid.

Example 2

Preparation of methyl (S)-2-(2-chlorophenyl)-2-(4,5,6,7-tetrahydrothieno[3,2-c]5-pyridyl)acetate (1)

Method 1

31.6 g (0.108 moles) of N,N"-bis-4,5,6,7-tetrahydro[3,2-c]-thienopyridyl methane (12) and 150 ml of acetonitrile are placed in a 500 ml three-necked round-bottom flask equipped with magnetic stirrer, condenser and dropping funnel. The resulting suspension is kept under nitrogen atmosphere and then refluxed. A solution consisting of 40 g (0.104 moles) of methyl (R)-2-(2-chlorophenyl)-2-(4-nitrobenzenesulfonyloxy)acetate (13a) dissolved in 150 ml of acetonitrile is then added in 1 hour 30 minutes. 1 Hr after the end of the addition, the mixture is cooled to −15° C. and the precipitated solid is filtered. The resulting clear solution is analyzed by HPLC (HPLC yield: 74%). The solvent is evaporated off under reduced pressure and the residue is taken up in toluene (about 600 ml) and treated with a 5% w/w sodium bicarbonate aqueous solution (100 ml). The organic phase is washed with 100 ml of water and filtered through decolourizing charcoal. The solvent is then removed under reduced pressure and the residue is taken up into 300 ml of acetone. The resulting clear solution is added with concentrated sulfuric acid to acid pH, while keeping temperature at 20° C. The mixture is stirred at room temperature for 12 hours, then the precipitated solid is recovered by filtration and washed with fresh acetone, thereby obtaining 23.92 g of clopidogrel hemisulfate (57.02 mmoles, yield=55%), which is identified by comparison.

Method 2

7.51 g (25.9 mmoles) of N,N'-bis-4,5,6,7-tetrahydro-[3,2-c]-thienopyridyl methane (12), 30 ml of acetonitrile and 3.57 g (25.9 mmol) of potassium carbonate are placed in a 250 ml three-necked round-bottom flask equipped with magnetic stirrer, condenser and dropping funnel. The resulting suspension is kept under nitrogen atmosphere and refluxed, then added with a solution consisting of 20 g (51.8 mmoles) of compound (13a) dissolved in 70 ml of acetonitrile, in 4 hours. 16 Hrs after the end of the addition, the mixture is cooled at room temperature, then after 1 hour the solid is filtered. According to HPLC analysis, the resulting clear solution contains g 7.5 of clopidogrel base (yield: 45%). The resulting product is then recovered as hemisulfate following the procedure described in Method 1.

Method 3

2.75 g (9.48 mmoles) of N,N'-bis-4,5,6,7-tetrahydro[3,2-c]-thienopyridyl methane (12) and 8 ml of acetonitrile are placed in a 25 ml three-necked round-bottom flask equipped with magnetic stirrer, condenser and dropping funnel. The resulting suspension is kept under nitrogen atmosphere and refluxed, then added with a solution consisting of 2.5 g (9.48 mmoles) of methyl (R)-2-bromo-(2-chlorophenyl)acetate (13b) dissolved in 8 ml of acetonitrile, in 1 hour 30 minutes. 2 Hrs 30 minutes after the end of the addition, the mixture is cooled at room temperature and the precipitated solid is filtered off. According to HPLC analysis, the resulting clear solution contains 1.95 g of clopidogrel base (yield: 64%). The resulting product is then recovered as hemisulfate following the procedure described in Method 1.

Method 4

3.76 g (12.97 mmoles) of N,N'-bis-4,5,6,7-tetrahydro[3,2-c]thienopyridyl methane (12) and 11 ml of acetone are placed in a 50 ml three-necked round-bottom flask equipped with magnetic stirrer and dropping funnel. The resulting suspension is added with a solution consisting of 2.5 g (6.48 mmoles) of compound (13a) in 9 ml of acetone in 40 minutes. 25 Hrs after the end of the addition, the precipitated solid is filtered off. According to HPLC analysis, the resulting clear solution contains 1.81 g of clopidogrel base (yield: 87%). The solvent is evaporated off under reduced pressure, the residue is taken up with toluene (30 ml) and the resulting solution is treated with decolorizing charcoal. The obtained clear solution is added with water (20 ml) and acetic acid to pH 3-4. The organic phase is separated, washed with water (20 ml) and concentrated to a residue under reduced pressure. The resulting oil is taken up into acetone, then clopidogrel (1) is isolated as hemisulfate following the procedure described in Method 1.

Method 5

3.76 g (12.97 mmoles) of N,N'-bis-4,5,6,7-tetrahydro-[3,2-c]-thienopyridyl methane (12) and 11 ml of acetone are placed in a 50 ml three-necked round-bottom equipped with magnetic stirrer, condenser and dropping funnel. The resulting suspension is refluxed while adding a solution consisting of 2.5 g (6.48 mmoles) of compound (13a) in 9 ml of acetone in 40 minutes. 2 Hrs after the end of the addition, the reaction mixture is cooled at room temperature, and the precipitated solid is filtered off after 1 hour. According to HPLC analysis, the resulting clear solution contains g 1.75 g of clopidogrel base (yield: 84%). Clopidogrel (1) is then isolated as hemisulfate following the procedure described in Method 4.

Method 6

1.88 g (6.48 mmoles) of N,N'-bis-4,5,6,7-tetrahydro-[3,2-c]-thienopyridyl methane (12), 11 ml of acetone and 0.84 g (6.48 mmol) of diisopropyl-ethyl-amine are placed in a 50 ml three-necked round-bottom equipped with magnetic stirrer, condenser and dropping funnel. The resulting mixture is refluxed while adding a solution consisting of 2.5 g (6.48 mmoles) of compound (13a) in 9 ml of acetone in 40 minutes. The resulting mixture is refluxed until completion of the reaction, then cooled at room temperature. According to HPLC analysis, the resulting clear solution contains 1.35 g of clopidogrel base (yield: 65%). The resulting product is then isolated as hemisulfate following the procedure described in Method 4.

Method 7

3.76 g (12.97 mmoles) of N,N'-bis-4,5,6,7-tetrahydro[3,2-c]thienopyridyl methane (12), 20 ml of methanol and 2.5 g (6.48 mmoles) of compound (13a) are placed in a 50 ml three-necked round-bottom flask equipped with magnetic stirrer, condenser and dropping funnel. The resulting suspension is refluxed for 1 hour 30 minutes. The resulting mixture is cooled at room temperature and kept at this temperature for 1 hour. The formed solid is filtered off. According to HPLC analysis, the resulting clear solution contains 1.65 g of clopidogrel base (yield 79%). Clopidogrel is then isolated as hemisulfate following the procedure described in Method 4.

The invention claimed is:

1. A process for the preparation of methyl [(S)-2-(2-chlorophenyl)-2-(4,5,6,7-tetrahydrothieno [3,2-c]-5-pyridyl)acetate] (1), or a pharmaceutically acceptable salt thereof,

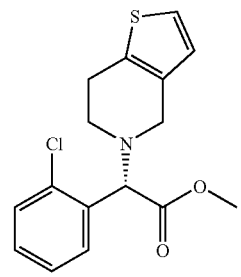

(1)

wherein said process comprises, reacting N,N'-bis-4,5,6,7-tetrahydro-[3,2-c]-thienopyridyl methane (12)

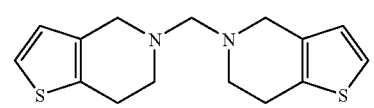

(12)

with a (R)-2-chlorophenylacetic acid derivative of formula (13)

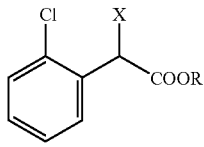

(13)

wherein:
R is a hydrogen atom or a straight or branched $C_1$-$C_4$ alkyl group,
and X is:
a halogen selected from fluorine, chlorine, bromine and iodine; a $OSO_2R^1$ group wherein $R^1$ is a straight or branched $C_1$-$C_4$ alkyl group, optionally substituted with one or more halogen atoms, a straight or branched $C_1$-$C_8$ perfluoroalkyl group, an aromatic ring optionally substituted with one or more halogen atoms, straight or branched $C_1$-$C_4$ alkyl groups, or nitro groups;
a $OCOR^1$ ester group in which $R^1$ has the meanings defined above;
a —$ONO_2$ group;
a $OP(OR)_2$ phosphite group or a $OPO(OR)_2$ phosphate group, in which R has the meaning as defined above; and,
if desired, salifying a compound of formula (I).

2. The process as claimed in claim 1 wherein a compound of formula (13) is selected from the group consisting of (R)-2-(2-chlorophenyl)-2-(4-nitrobenzenesulfonyloxy)acetic acid methyl ester and (R)-2-bromo-2-(2-chlorophenyl)acetic acid methyl ester.

3. The process as claimed in claim 1 wherein the reaction is carried out in a protic or aprotic organic solvent, and, if the case, in the presence of a basic agent.

4. The process as claimed in claim 1 wherein the molar ratio of compound of formula (12) to intermediate of formula (13) ranges from 0.5:1 to 3:1.

5. The process as claimed in claim 3 wherein the organic solvent is selected from the group consisting of a ketone, an alcohol, acetonitrile, an aromatic hydrocarbon and a chlorinated solvent.

6. The process as claimed in claim 3 wherein the basic agent is an organic base selected from the group consisting of N,N'-bis-4,5,6,7-tetrahydro-[3,2-c]-thienopyridyl methane, diisopropyl-ethyl-amine, 4-(dimethylamino)pyridine, triethylamine, 1,8-diazabicyclo[5.4.0]undec-7-ene, and 1,4-diazabicyclo [2.2.2]octane.

7. The process as claimed in claim 5 wherein the organic base is N,N'-bis-4,5,6,7-tetrahydro-[3,2-c]-thienopyridyl methane.

8. The process as claimed in claim 3 wherein the basic agent is an inorganic base selected from the group consisting of an alkali and alkaline-earth metal carbonate.

9. The process as claimed in claim 1 wherein the reaction temperature ranges from 0° C. to the reflux temperature of the solvent.

10. Compound N,N'-bis-4,5,6,7-tetrahydro-[3,2-c]-thienopyridyl methane (12)

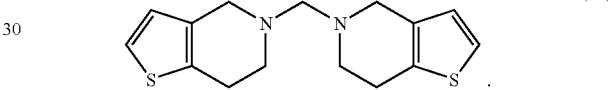

(12)

* * * * *